United States Patent
Ubieta Gómez et al.

(10) Patent No.: US 9,205,130 B2
(45) Date of Patent: Dec. 8, 2015

(54) ORALLY ADMINISTRABLE PHARMACEUTICAL PELLET OF EPIDERMAL GROWTH FACTOR

(75) Inventors: Raimundo Ubieta Gómez, Ciudad de la Habana (CU); Ana Aguilera Barreto, San Agustin Lisa (CU); Eduardo Martínez Díaz, Ciudad de la Habana (CU); Rolando Paez Meireles, Ciudad de la Habana (CU); Antonio Sereno Guerra, Melsbroeck (BE)

(73) Assignees: CENTRO DE INGENIERIA GENETICA Y BIOTECNOLOGIA, Ciudad de la Havana (CU); BIOREC S.A., Montevideo (UY)

( * ) Notice: Subject to any disclaimer, the term of this patent is extended or adjusted under 35 U.S.C. 154(b) by 0 days.

(21) Appl. No.: 13/578,211

(22) PCT Filed: Feb. 10, 2011

(86) PCT No.: PCT/EP2011/051918
§ 371 (c)(1),
(2), (4) Date: Aug. 9, 2012

(87) PCT Pub. No.: WO2011/098499
PCT Pub. Date: Aug. 18, 2011

(65) Prior Publication Data
US 2012/0308661 A1  Dec. 6, 2012

(30) Foreign Application Priority Data
Feb. 12, 2010 (EP) ..................................... 10382033

(51) Int. Cl.
| A61K 9/50 | (2006.01) |
| A61P 1/04 | (2006.01) |
| B05D 7/00 | (2006.01) |
| A61K 38/18 | (2006.01) |
| A61K 9/48 | (2006.01) |
| A61K 47/38 | (2006.01) |
| A61K 47/18 | (2006.01) |
| A61K 47/02 | (2006.01) |

(52) U.S. Cl.
CPC ............... *A61K 38/1808* (2013.01); *A61K 9/48* (2013.01); *A61K 9/50* (2013.01); *A61K 9/5026* (2013.01); *A61K 9/5078* (2013.01); *A61K 47/02* (2013.01); *A61K 47/183* (2013.01); *A61K 47/38* (2013.01)

(58) Field of Classification Search
None
See application file for complete search history.

(56) References Cited

U.S. PATENT DOCUMENTS

| 4,743,679 A | * | 5/1988 | Cohen et al. | 530/350 |
| 5,272,135 A | * | 12/1993 | Takruri | 514/2.4 |
| 2005/0112193 A1 | * | 5/2005 | Phillips et al. | 424/464 |
| 2007/0026082 A1 | * | 2/2007 | Lizio et al. | 424/490 |
| 2010/0068210 A1 | * | 3/2010 | Ji et al. | 424/141.1 |

FOREIGN PATENT DOCUMENTS

| EP | 0262326 B1 | * | 7/1987 |
| JP | S62149622 A | | 7/1987 |
| JP | H01246223 A | | 10/1989 |
| JP | 2006503045 A | | 1/2006 |
| JP | 2006513983 A | | 4/2006 |
| JP | 2007513983 A | | 5/2007 |
| JP | 2005527470 A | | 6/2010 |
| WO | WO 99/30671 | * | 1/1999 |
| WO | WO03020299 A1 | | 3/2003 |
| WO | WO2004000347 A1 | | 12/2003 |
| WO | WO2004024125 A1 | | 3/2004 |
| WO | WO2005058345 A1 | | 6/2005 |
| WO | WO2007095288 A2 | | 8/2007 |
| WO | WO2008056967 A1 | * | 5/2008 |
| WO | WO2010030670 A2 | | 3/2010 |

OTHER PUBLICATIONS

English language translation of EP 0262326 B1.*
English language translation of WO 2008/056967 A1.*
Sule Coskun et al., Effects of Epidermal Growth Factor on lipid peroxidation and Nitric Ocide levels in oral mucosal ulcer healing: a time-course study, Jun. 2007, pp. 570-574, vol. 37, No. 7, Surgery Today; Official Journal of the Japan Surgical Society, Springer-Verlag.
Dorkoosh F.A. et al, Peroral drug delivery systems for peptides and proteins, Jan. 2002, pp. 213-221, vol. 12, Issue 4, Sciences Techniques et pratiques STP Pharma Sciences, Paris, FR.
Han Kun et al., Site-specific degradation and transport of recombinant human epidermal growth factor (rhEGF) in the rat gastrointestinal mucosa, Jun. 1998, pp. 189-197, vol. 168, No. 2, International Journal of Pharmaceutics Amsterdam.
International Search Report and Written Opinion of the International Searching Authority, or Declaration Application No. PCT/EP2011/051918 issued by the European Patent Office, Rijswijk, Netherlands, dated Jul. 8, 2011.
English Translation of Notice of Reasons for Rejection issued by the Japanese Patent Office in counterpart foreign application No. 2012-552388, date mailed: Sep. 30, 2014.

(Continued)

*Primary Examiner* — Rachael E Bredefeld
*Assistant Examiner* — Dominic Lazaro
(74) *Attorney, Agent, or Firm* — Peter B. Scull; Hamilton, DeSanctis & Cha LLP

(57) ABSTRACT

The present invention comprises a pellet of epidermal growth factor and methionine or $K_2S_2O_7$, a capsule which comprises these pellets, processes for theirs preparations and it use for the treatment of ulcerative colitis.

16 Claims, No Drawings

(56) References Cited

OTHER PUBLICATIONS

Liu Wentian, "The study of gastrointestinal hormones and epidermal growth factor in the mechanism of action of ulcerative colitis", Dec. 23, 1996, pp. 516-518, China Academic Journal Electronic Publishing House, Beijing, China.

English abstract, Liu Wentian, "The study of gastrointestinal hormones and epidermal growth factor in the mechanism of action of ulcerative colitis", Dec. 23, 1996, pp. 516-518, China Academic Journal Electronic Publishing House, Beijing, China.

* cited by examiner

//ORALLY ADMINISTRABLE PHARMACEUTICAL PELLET OF EPIDERMAL GROWTH FACTOR

CROSS REFERENCES TO RELATED APPLICATIONS

This application is a national stage filing under 35 USC 371 of international application no. PCT/EP2011/051918, filed 10 Feb. 2011 and published on 18 Aug. 2011 under international publication no. WO 2011/098499, which claims priority to EP 10382033.8 filed 12 Feb. 2010. Both are hereby incorporated by reference as though fully set forth herein.

FIELD OF THE INVENTION

The present invention relates to an oral administrable pharmaceutical pellet of epidermal growth factor (EGF), to capsules containing it, to their preparations processes and their use for the treatment of ulcerative colitis.

BACKGROUND ART

Ulcerative colitis (UC) is a form of an inflammatory bowel disease (IBD) with a presumed genetic component. This produces an abnormal response of the immune system against intraluminar antigens whose main symptom is a chronic inflammation of the gastrointestinal tract accompanied by tissular destruction.

Although there is not a cure for UC, dietary modification may reduce the discomfort of a person with the disease and besides, the treatment with medicaments which can stabilize the patient are also indicated. Medicaments such as anti-inflammatory drugs (i.e. 5-aminosalicylate and corticosteroids), antibiotics and immunomodulators (i.e. azathioprine, 6-mercaptopurinam, cyclosporine and metotrexate), and immunosuppressant agents are commonly used. A disadvantage of these medicaments is that induce an unspecific suppression of the inflammatory process which provoke gastrointestinal side-effects such as nausea, diarrhea, abdominal pain, headache, and decrease of the immunoresponse of the patient. These gastrointestinal side-effects increase the risk of suffering infections, leucocytopenia or hepatic and pancreatic alterations, as well as osteoporosis, muscular dystrophy and weakness in long-term treatment with corticosteroids.

The treatment of UC is mainly based in the use of 5-aminosalicylic acid (5-AAS) as an active ingredient. A problem of the treatment with 5-AAS is the poor absorption of the active ingredient in the colon tract which provoke that the effective therapeutic concentrations are difficult to achieve. Therefore, it has been designed new formulations of 5-AAS which increase the absorption of the active ingredient. These formulations include microspheres, dimers or conjugates of 5-AAS which unfortunately continue maintaining the same gastrointestinal side-effects.

An alternative treatment for the restoration of the tissular damage in UC is the administration of peptides, in particular cytoprotective factors which are naturally secreted into the intestinal mucosa to restore its integrity. These factor can be alpha and beta transforming growth factor (TGF), trefoil factor, epidermal growth factor (EGF), keratinocyte growth factor (KGF), interleukin 11 (IL11), and a growing factor.

Control release formulations of some cytoprotective factors for their oral administration for its released in the intestinal lumen are known in the art. Thus, US 2007/26082 discloses an oral multiparticle pharmaceutical pellet which is form by an inner matrix layer containing peptides embedded in a matrix formed by a polymer with a mucoadhesive features.

The EGF is a growth factor that plays an important role in the regulation of growth, proliferation, and differentiation of cells by its binding to the epidermal growth factor receptor (EGFR). Human EGF is a 6045-Da protein with 53 amino acid residues and three intramolecular disulfide bonds. The high affinity binding of EGF to EGFR on the cell surface stimulates the intrinsic protein-tyrosine kinase activity of the receptor. The tyrosine kinase activity initiates a signal transduction cascade that results in a rise in the intracellular calcium levels, increases glycolysis and protein synthesis, and also increases the expression of certain genes including the gene for EGFR which results in the DNA synthesis and cell proliferation.

The EGF has been previously used in therapy. For example, EGF has been orally administered for its cicatrizing effect in gastro-duodenal lesions because the EGF acts before being degraded by the acidic conditions of the stomach. Besides, the EGF has been used for the treatment of UC only when administering via enema. This via has shown not to be effective in the treatment of UC in the ascendant portion of the colon tract. Besides, the subcutaneous administration of EGF alone or in combination with trefoil factor had shown its effectively in the restoration of wound and the treatment of UC.

EGF due to its peptide nature can modify spontaneously its structure during long-term packaging or in contact with biological fluids. This modification can compromises its half life and biological activity. The most probable ways of degradation of EGF are the oxidation of methionine residues, the desamination of asparagine residues and the formation of the succinamide in the position of aspartic acid residues. Besides, the exposure of EGF to some excipients during manufacturing conditions or storage of a pharmaceutical formulation, that is temperature, time, radiation intensity or humidity can provoke the denaturalisation of the ternary and quaternary structure (native structure) or fragmentation of the peptide chain promoting the response of the immune system against the EGF.

From what is known in the art it is derived that there is still the need of providing stable oral pharmaceutical compositions of epidermal growth factor where the active ingredient has a controlled release in the entire tract of the colon after a rapid passage through the stomach.

SUMMARY OF THE INVENTION

Inventors have found that a pharmaceutical pellet for oral administration comprising the epidermal growth factor and methionine or potassium pyrosulphate ($K_2S_2O_7$) as antioxidant, has an appropriate dissolution profile and shows a good stability of the active ingredient being protected from physical or proteolytic inactivation. Besides, it is advantageous because of its extended timing uptake, the reduction of the risk of gastro-intestinal side-effects, the reduction of the treatment and the better acceptance by the patients of the oral administered posologies.

Thus, an aspect of the present invention refers to an oral administrable pharmaceutical pellet which comprises a core and an enteric coating, wherein the core comprises the EGF and a sulphur-containing antioxidant selected from methionine and potassium pyrosulphate. Both antioxidants are solids soluble in water. Both antioxidants have ionic character, the methionine is in switerionic form at neutral pH, that means that contain an anionic center and a cationic center in the same molecule and the potassium pyrosulphate is an ionic salt composed of potassium cations and pyrosulphate anions.

Another aspect of the present invention refers to a process for the preparation of the pellet as defined above, which comprises: (a) coating of the inert nucleus by spraying an aqueous suspension comprising the epidermal growth factor, the antioxidant and pharmaceutically acceptable excipients; (b) drying the active layer formed in step (a); (c) coating the coated nucleus of step (b) by spraying a suspension comprising a enteric coating polymer and pharmaceutically acceptable excipients; (d) drying the coating pellet formed in step (c); where the temperature of each step of the process is up to 40° C.

Another aspect of the present invention relates to a pharmaceutical capsule which comprises the pellets as defined above.

Finally, another aspect of the present invention relates to the pharmaceutical pellet of the present invention for use in the treatment of ulcerative colitis.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "molar ratio" refers to the relation of moles of epidermal growth factor with the moles of antioxidant needed to protect the active ingredient from degradation or inactivation.

The term "binder" refers to a material which imparts cohesiveness to powdered materials improving free-flowing qualities in the manufacture of tablets or pellets. Materials commonly used as binders include starch, gelatine, sugars, sodium alginate, carboxymethylcellulose, methylcellulose or polyvinylpyrrolidine.

The term "alkaline agent" can be selected from a compound with alkaline reaction, such as sodium; potassium; calcium; magnesium and aluminium salts of phosphoric acid, carbonic acid, citric acid; aluminium/magnesium mixed compounds of $Al_2O_3.6MgO.CO_2.12H_2O$ or $MgO.Al_2O_3.2SiO_2.nH_2O$ where n is a whole integer of 2 or more, or similar compounds and amino acids with alkaline reaction. In addition the alkaline material may be antacid materials such as aluminium hydroxides, calcium hydroxides, magnesium hydroxides or magnesium oxide.

The term "glidant" refers to a material which improves the flow characteristics of powder mixtures in the dry state. Materials commonly used as a glidant include magnesium stearate, colloidal silicon dioxide or talc.

The term "surfactant" refers to a material which lowers the surface tension of a liquid and the interfacial tension between two liquids, allowing their easier spreading. Materials commonly used as a surfactant include sodium lauryl sulphate (LSS) or diethylene glycol monoethylether.

The term "percentage (%) by weight" refers to the percentage of each ingredient of the pharmaceutical composition in relation to the total weight of the pellet.

The term "inert nucleus" refers to microspheral neutral granules which can have in their composition one or more of the following substances: sorbitol, mannitol, sacharose, starch, microcrystalline cellulose, lactose, glucose, trehalose, maltitol or fructose. The initial size of this inert nucleus can be between 200 and 1800 micrometers.

The term "human epidermal growth factor" refers to the EGF having that polypeptide sequence, or any substantial portion thereof. Human EGF also refers to any human EGF variants, such as gamma-urogastrone. EGF may be isolated from natural sources, produced using recombinant DNA techniques or prepared by chemical synthesis. It is contemplated that biologically active fragments, analogs or man-made chemically synthesized derivatives of EGF may be used in the present invention instead of the entire naturally occurring molecule, provided that such fragments, analogs or derivatives retain the biological activity of naturally occurring EGF. As used herein, EGF includes the EGF produced by any of the aforementioned methods and any bioactive fragments, analogs or derivatives and related polypeptides thereof.

The term "analog" of EGF refers to any polypeptide having a substantially identical amino acid sequence to EGF in which one or more amino acids have been substituted with chemically similar amino acids. The term "analog" shall also include any polypeptide which has one or more amino acids deleted from or added to the EGF polypeptide, but which still retains a substantial amino acid sequence homology to EGF. A substantial sequence homology is any homology greater than 50 percent. The term "fragment" of EGF refers to any shorter version of EGF having at least 10 amino acid residues and having the same bioactivity as EGF. The phrase "chemical derivative" refers to any polypeptide derived from the naturally occurring EGF polypeptide in which one or more amino acids have been chemically derivatized synthetically by reaction of functional side groups of the amino acids (i.e. it is derived from the parent EGF molecule by one or more steps).

A "pharmaceutically effective amount" of EGF refers to that amount which provides a therapeutic effect in various administration regimens.

The term "enteric coating" refers to any pharmaceutically acceptable coating preventing the release of the active ingredient in the stomach.

The term "polymer" refers to a molecule containing a plurality of covalently attached monomer units, and includes branched, dendrimeric, star, and linear polymers. The term also includes homopolymer and copolymers, as well as uncrosslinked polymers and from slightly to moderately or substantially crosslinked polymers.

Terms "modified release polymer" and "modified delivery polymer" have the same meaning and are interchangeable. Both terms are to be understood as polymers which allow the delivery of the drug at a predetermined rate and/or location according to the needs of the body and disease states for a definite time of period. Illustrative but non-limitative examples of "modified release polymer" and "modified delivery polymer" are polymers which provide a controlled release, a sustained release, a prolonged release or an extended release.

As mentioned above, an aspect of the present invention refers to an oral administrable pharmaceutical pellet which comprises a core and an enteric coating, wherein the core comprises the epidermal growth factor and a sulphur-containing antioxidant selected from the group consisting of methionine and $K_2S_2O_7$.

The composition of the core of the pellet allows having effective concentrations in the entire of the intestinal tract. The outer coating avoids the hydrolysis of the EGF in the stomach and allows the EGF achieving the targeting site of the intestinal tract in its native and active conformation. In consequence, the EGF is stable during the preparation process of the pharmaceutical composition, during packaging, and after the administration. This is advantageous because generally peptides can be degraded by the oxidation of certain residues of the peptide chain in the presence of oxygen, being especially susceptible to degradation conditions when they are in liquid form formulations due to the fact that they are usually packaged in plastic containers permeable to oxygen.

The target dissolution profile comprises that less than 3% of EGF in 2 hours is dissolved when it is submitted to stomach conditions (i.e. HCl 0.1N) and at least more than 60% of the EGF after 6 hours is dissolved when it is submitted to colon conditions (buffered step) (cf. Example 4 Table 3).

Therefore, the required controlled dissolution profile of EGF maintaining its effective therapeutical concentrations in the entire intestinal tract after its oral administration, is achieved by a pellet which comprises a core and an outer enteric coating, where the core comprises an inner active layer containing the epidermal growth factor and sulphur-containing antioxidant selected from the group consisting of methionine and $K_2S_2O_7$ around an inert nucleus.

In a preferred embodiment, the molar ratio between the EGF and the antioxidant as defined above is from 1:10 to 1:670. In a more preferred embodiment the molar ratio is from 1:15 to 1:100. In another preferred embodiment the molar ratio is from 1:20 to 1:80. In another more preferred embodiment the molar ratio is from 1:25 to 1:60. Preferably, the molar ratio between EGF and methionine is 1:30 and the molar ratio between EGF and $K_2S_2O_7$ is 1:30. The mentioned molar ratio between the active ingredient and the antioxidant contributes to ensure the EGF stability in the pellets of the present invention in order to maintain its native conformation.

The pellets of the present invention can contain additional pharmaceutical excipients. The excipients must be selected from those that do not degrade the epidermal growth factor in order to prepare the orally administrable pharmaceutical pellets of the invention.

In a preferred embodiment, the core of the pellet further comprises a binder, an alkaline agent, a glidant, a surfactant, or mixtures thereof. Pellets of the present invention could be formed by excipients which helps the formation of the active layer around the inert nucleus.

In a particular embodiment the binder is selected from the group consisting of methylcellulose, carboxymethylcellulose, hydroxypropylmethylcellulose, hydroxypropylcellulose, and polivinylpirrolidone. In a preferred embodiment the binder is hydroxypropylmethylcellulose (HPMC).

In a particular embodiment the alkaline agent is selected from the group consisting of magnesium carbonate, N-methyl glutamine, disodium phosphate, and calcium phosphate. In a preferred embodiment the alkaline agent is disodium phosphate.

In a particular embodiment the glidant is selected from the group consisting of magnesium stearate, glicerylmonoestearate, colloidal silicon dioxide, stearic acid, talc, and sodium stearyl fumarate. In a preferred embodiment the glidant is talc.

In a particular embodiment the surfactant is selected from the group consisting of sodium lauryl sulphate, and diethylene glycol monoethylether. In a preferred embodiment the surfactant is sodium lauryl sulphate.

In a preferred embodiment the core of the pellet of the present invention comprises: 60-80% by weight of the inert nucleus; 0.05-1% by weight of the epidermal growth factor; 0.5-3% by weight of antioxidant; 0.02-0.07% by weight of surfactant; 1.5-5% by weight of binder; 0.02-0.07% by weight of alkaline agent; and 2-5% by weight of glidant.

In a more preferred embodiment the core of the pellet comprises: 69% by weight of the inert nucleus; 0.10% by weight of the epidermal growth factor; 1.3% by weight of methionine; 0.05% by weight of sodium lauryl sulphate; 2% by weight of hydroxypropylmethylcellulose; 0.05% by weight of disodium phosphate; and 4% by weight of talc.

In another preferred embodiment the core of the pellet comprises: 69% by weight of the inert nucleus; 0.10% by weight of the epidermal growth factor; 2% by weight of $K_2S_2O_7$; 0.05% by weight of sodium lauryl sulphate; 2% by weight of hydroxypropylmethylcellulose; 0.05% by weight of disodium phosphate; and 4% by weight of talc.

As it is illustrated in the examples, the content of EGF in solutions of the active ingredient with one excipient from those mentioned above or combinations thereof is maintained above 90% by weight even after 30 days of being storage at 37° C. protected from the light (cf. Table 5). The EGF is especially easily oxidized by air in liquid solution. As only about 10% of the EGF in the tested solutions was degraded by the excipients mentioned in Example 1, it is considered that the excipients used for the preparation of the pellets of the present invention are not responsible for the oxidation of the EGF. (cf. Example 5)

As mentioned above the pellets of the present invention are coated with an enteric coating. Example of appropriate gastro-resistant polymers to prepare the enteric coating include methylcellulose, hydroxyethylcellulose (HEC), hydroxybutylcellulose (HBC), hydroxypropylmethylcellulose (HPMC), ethylcellulose, hydroxymethylcellulose (HMC), hydroxypropylcellulose (HPC), polyoxyethylene glycol, castor oil, cellulose phthalic acetate, phthalate of HPMC, succinate acetate of HMC, sodium carboxymethylamylopectin, chitosan, alginic acid, carrageenans, galactomannons, tragacanth, shellac, agar-agar, gum arabic, guar gum and xanthan gum, polyacrylic acids, polyvinyl alcohol (PVA), polyethylene and polypropylene oxides or mixtures thereof. Others appropriate compounds include gastro-resistant polymers based on methacrylics or their salts such as an anionic copolymer based on methyl acrylate, methyl methacrylate, and methacrylic acid (Eudragit FS30D), an anionic copolymer based on methacrylic acid, and methyl methacrylate (Eudragit S100), or a copolymer of acrylic and methacrylic acid esters and quaternary ammonium groups (Eudragit RS or Eudragit RL). Preferably the enteric coating polymer is Eudragit FS30D.

The gastro-resistant polymer can be accompanied by plasticizers such as triethylcitrate (TEC), polyethylene glycol (PEG), cetyl, and stearyl alcohol; surface-active agents such as sodium lauryl sulphate, polysorbate, and poloxamer; pigments such as titanium dioxide or iron sesquioxide; lubricants such as talc, magnesium stearate or glyceril monostearate, and mixtures thereof.

In a preferred embodiment the enteric coating comprises poly(methacrylic acid/methylacrylate/methyl methacrylate), triethylcitrate, sodium lauryl sulphate, talc or mixtures thereof.

In a preferred embodiment the enteric coating layer is from 14 to 25% by weight of the total weight of the pellet of the present invention.

In a particular embodiment, the pellets of the present invention further comprise an intermediate coating layer between the core and the enteric coating. This intermediate coating layer comprises at least a modified release polymer. Appropriate modified release polymers for preparing the intermediate coating layer include, but are not limited to, acrylic polymers, celluloses, shellac, zein, hydrogenated vegetable oil, hydrogenated castor oil, and their mixtures. Examples of suitable acrylic polymers include, but are not limited to, acrylic acid and methacrylic acid copolymers, methyl methacrylate copolymers, ethoxyethyl methacrylates, cyanoethyl methacrylate, aminoalkyl methacrylate copolymer, poly (acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and their mixtures. Examples of suitable celluloses include ethylcellulose, hydroxypropylcellulose, hydroxypropylmethylcellulose, and their mixtures.

Modified release polymers is selected from the group consisting of acrylic acid and methacrylic acid copolymers such as Eudragit L, Eudragit S, Eudragit FS, Eudragit RS, Eudragit RL, Eudragit RD, and Eudragit NE. Preferably, the modified release polymer is Eudragit NE 30D.

The modified release polymers can be accompanied by plasticizers such as triethylcitrate (TEC), polyethylene glycol (PEG), cetyl and stearyl alcohol; surface-active agents such as sodium lauryl sulphate, polysorbate and poloxamer; pigments such as titanium dioxide, iron sesquioxide; lubricants such as talc, magnesium stearate or glyceril monostearate, and mixtures thereof.

In a particular embodiment the intermediate coating layer further comprises a glidant. Preferably, the glidant is talc.

In a preferred embodiment the intermediate coating layer is from 5 to 20% by weight of the total weight of the pellet of the present invention. Preferably, the weight of the intermediate coating layer is 15%.

Due to the instability of the EGF in the presence of oxygen or high humidity, when exposure to elevated temperature, high pressure, or when submitted to long times of manufacturing of the pharmaceutical formulation, the EGF is prepared by those conventional processes which does not produce degradation, having a control of the conditions of all steps of the process. The process for the manufacturing of the pellets of the present invention comprises in a first step, coating the inert nucleus by spraying an aqueous suspension of the EGF, the antioxidant and the appropriate excipient, avoiding high temperatures and prolonged exposure of the aqueous suspension of the active ingredient with the oxygen where the EGF could be degraded; and a second step of coating the active pellet as defined above with a enteric coating suspension. In both steps of the process the temperature should be not higher than 40° C. If the EGF is subjected to temperatures above 40° C. the peptidic bonds are broken and thereof the EGF loses its native structure and as a consequence its therapeutic activity. In a particular embodiment temperature of the process is from 27 to 40° C. Preferably, the temperature of the process is from 35° C. to 40° C. More preferably, the temperature of the process is 40° C.

Thus, the oral administrable pharmaceutical pellets of the invention can be prepared by a process which comprises: (a) coating of the inert nucleus by spraying an aqueous suspension, which comprises the epidermal growth factor, the antioxidant and the pharmaceutically acceptable excipients; (b) drying the active layer formed in step (a); (c) coating the nucleus of step (b) by spraying a suspension which comprises the enteric coating polymer and the pharmaceutically acceptable excipient; (d) drying the coating pellet formed in step (c); where the temperature of each step of the process is up to 40° C.

In a particular embodiment, the oral administrable pharmaceutical pellets of the invention which comprises the intermediate coating layer can be prepared by the process mentioned above, further comprising an additional step of coating the nucleus obtained in step (b) by spraying a suspension which comprises the modified release polymer and the pharmaceutically acceptable excipient; and drying the layer formed.

In a particular embodiment, in order to obtain lower humidity content in the pellets of the present invention, the drying step (d) comprises drying the pellets obtained in step (c) in a plate dryer for 24 hours with air at a temperature of 40° C.

In another particular embodiment, all steps of the process as defined above are performed in a fluidized bed coater such as a "Wurster" type or similar into which the inert nucleus and the spraying aqueous active suspension and entering coating suspension are successively added.

As mentioned above, another aspect of the present invention is a pharmaceutical capsule which comprises pellets as defined above. The pharmaceutical composition can be prepared by any capsule filling method known in the state of the art. Thus, a process for preparing the pharmaceutical capsule comprises: (a) preparing the enteric coating pellet with EGF and antioxidant as defined above; (b) filling the pharmaceutical capsule with pellets of step (a); and optionally, (c) sealing the pharmaceutical capsule.

In a particular embodiment, the pharmaceutically acceptable amount of EGF is between 200 to 800 μg per capsule. Preferably, the amount of EGF is 500 μg per capsule.

The content of EGF in the capsules of the invention is stable. As it is illustrated in the examples it is maintained above 96% by weight when these capsules are packaged in blisters and stored at temperatures from 2 to 8° C. Besides, the organoleptic properties of the pharmaceutical composition are not modified and the humidity of the capsules is maintained below 1%. Thus, the EGF is neither degraded during the process of preparation of pellets and nor in the storage of the capsules (cf. Example 2 Table 1).

The capsules of the present invention also achieve the target dissolution profile. Thus, less than 3% of EGF is dissolved in 2 hours when it is submitted to stomach conditions (i.e. HCl 0.1N) and at least more than 60% of the EGF after 6 hours is dissolved when it is submitted to colon conditions (buffered step) (cf. Example 4 Table 3). The low dissolution percentage of EGF in the stomach avoids the degradation of the EGF by the proteolytic enzymes. On the other hand, rapid dissolution of EGF when the enteric coating is dissolved achieves effective concentration in the entire intestinal tract and the gastrointestinal side-effects for the administration of unspecific anti-inflammatory drugs are decreased.

As mentioned above, it is also part of the invention the pharmaceutical pellet defined above for use in the treatment of ulcerative colitis, in particular the restoration of the tissular damage of the entire intestinal tract in UC. This aspect could be also formulated as the use of the oral administrable pharmaceutical pellet as defined above for the preparation of a medicament for the treatment of ulcerative colitis or as a method for treating ulcerative colitis which comprises administering to mammals in need of such treatment an effective amounts of the pellet of the present invention. Thus, as it is shown in the results of the Example 3 Table 2, the activity of EGF is maintained after being formulated in form of capsules.

Throughout the description and claims the word "comprise" and variations of the word, are not intended to exclude other technical features, additives, components, or steps.

Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1

Process for Manufacturing Capsules of Pellets of Epidermal Growth Factor 1.1. Process for the Manufacture of the Enteric-Coating Pellet with Methionine The pellet composition is as follow:

Core Pellet

| Ingredients | (%) | Amount (g) | Amount dry substance (g) |
|---|---|---|---|
| Inert nucleus | 69.51 | 700 | |
| Epidermal growth factor (EGF) | 0.10 | 848.5 | 1.00 |
| methionine | 1.26 | | 12.65 |
| Sodium lauryl sulphate | 0.05 | 0.5 | |
| Hydroxypropylmethylcellulose | 1.99 | 20.0 | |
| disodium phosphate | 0.05 | 0.5 | |
| talc | 3.97 | 40.0 | |
| Total core weight | 76.94 | | 774.7 |

Enteric-Coating

| Ingredients | (%) | Amount (g) | Amount dry substance (g) |
|---|---|---|---|
| Polisorbate 80 | 0.06 | 0.6 | |
| Triethylcitrate | 0.12 | 1.2 | |
| Sodium lauryl sulphate | 0.12 | 1.2 | |
| Talc | 4.58 | 46.1 | |
| Eudragit FS30D | 18.20 | 610.9 | 183.3 |
| Purified water* | | q.s. | |
| Total coating weight | 23.08 | | 232.4 |
| Total functional pellets | 100 | | 1007.1 |

"q.s" means "as needed";
*Water removed after processing

In a stainless steel receptacle an aqueous solution of hydroxypropylmethylcellulose was prepared, and a solution of epidermal growth factor and methionine with a continuous agitation was added. When the mixture was homogeneous the sodium lauryl sulphate, disodium phosphate and talc were added, maintaining agitation at room temperature until homogeneity of the suspension.

700 g of inert nucleus were incorporated in a fluid bed and was covered with the suspension prepared in advance, under the following conditions: air flow: 260 m³/h, diameter of nozzles: 1 mm, spraying pressure: 0.7 bar, spraying of the suspension: 35 g/min., air temperature: 50° C. and product temperature: 35° C.

In a stainless steel receptacle an aqueous homogeneous dispersion of Polisorbate 80, triethylcitrate, and Eudragit FS30D was prepared, and the sodium lauryl sulphate and talc was added, maintaining agitation at room temperature until homogeneity of the suspension.

Dry cores were subjected to enteric coating by spraying the enteric aqueous suspension prepared above. The working conditions were as follows: air flow: 180 m³/h, diameter of nozzles: 1.2 mm, spraying pressure: 0.6 bar, spraying of the suspension: 30 g/min., air temperature: 55° C. and product temperature: 35° C.

The enteric coating pellets thus obtained were then dried in a plate dryer for 24 hours with air at a temperature of 40° C.

1.2. Process for the Manufacture of the Enteric-Coating Pellet with $K_2S_2O_7$

The pellet composition is as follow:

Core Pellet

| Ingredients | (%) | Amount (g) | Amount dry substance (g) |
|---|---|---|---|
| Inert nucleus | 68.72 | 700 | |
| Epidermal growth factor (EGF) | 0.10 | 848.5 | 1.00 |
| $K_2S_2O_7$ | 2.12 | | 21.55 |
| Sodium lauryl sulphate | 0.05 | 0.5 | |
| Hydroxypropylmethylcellulose | 1.96 | 20.0 | |
| disodium phosphate | 0.05 | 0.5 | |
| talc | 3.93 | 40.0 | |
| Total core weight | 76.93 | | 783.6 |

Enteric-Coating

| Ingredients | (%) | Amount (g) | Amount dry substance (g) |
|---|---|---|---|
| Polisorbate 80 | 0.06 | 0.6 | |
| Triethylcitrate | 0.12 | 1.2 | |
| Sodium lauryl sulphate | 0.12 | 1.2 | |
| Talc | 4.58 | 46.6 | |
| Eudragit FS30D | 18.20 | 617.9 | 181.7 |
| Purified water* | | q.s. | |
| Total coating weight | 23.08 | | 235.1 |
| Total functional pellets | 100 | | 1018.7 |

"q.s" means "as needed";
*Water removed after processing

These pellets were prepared analogously to the pellets of the previous section (1.1.) by using $K_2S_2O_7$ as antioxidant.

Process for the Manufacture of Capsules

Hard capsules made of gelatin or hydroxypropylmethylcellulose with the enteric-coating pellets were filled using a Bosch Zanassi automatic capsule-filling machine.

Example 2

Stability Studies

The physical and chemical stability of epidermal growth factor in capsules of Example 1 packaged in blisters at a temperature of 5±3° C. for a period of 24 months were tested.

The analysis of the organoleptic properties of capsules of example 1 did not showed any modification of their appearance. The humidity of capsules of Example 1 tested by Karl Fisher method was maintained below 1%.

For determining the content of epidermal growth factor in the capsules of the present invention, 100 ml of phosphate saline buffer (PBS1x) were added to the content of 10 capsules of example 1, maintaining agitation for 15 minutes. The resultant suspension was centrifuged for 5 minutes at 9000 rpm and the aqueous solution was collected and quantified by high performance liquid chromatography (HPLC).

TABLE 1

Content of epidermal growth factor in capsules of Example 1

| Test time (Months) | EGF (%) | | |
|---|---|---|---|
| | Batch PFCE-1 | Batch PFCE-2 | Batch PFCE-3 |
| 0 | 98.02 | 97.56 | 98.48 |
| 3 | 97.63 | 97.87 | 98.34 |
| 6 | 97.80 | 97.07 | 97.18 |
| 9 | 97.29 | 96.06 | 98.37 |
| 12 | 97.03 | 97.52 | 97.16 |
| 18 | 97.54 | 96.87 | 98.18 |
| 24 | 97.32 | 96.25 | 97.34 |

The previous results in Table 1 show that the epidermal growth factor is stable in the pellets of the present invention where these pellets are introduced into capsules, packaged in blisters and stored at temperatures from 2 to 8° C. The small variability observed in the content of EFG in the previous Table 1 is due to the experimental error of the analytical method used.

The content of EGF in pellets without methionine or $K_2S_2O_7$ in the core is less than 85% and the degradation of the EGF in 24 months is about 15%. In comparison, as it is illustrated in Table 1 the degradation of EGF in 24 months in the pellets of the present invention is about 4%, thus as the content of the active ingredient is above 96%, the pellets of the present invention are considered stable.

Example 3

Biological Activity

The activity of epidermal growth factor in capsules of example 1 packaged in blisters and stored at temperatures of 5±3° C. were tested. This biological test is based on the capacity of the epidermal growth factor human recombinant (EGF Hu-r) to induce the proliferation of cell lines of mouse embryos of 3T3/A3 which are extremely sensitive to contact inhibition cell division.

Biological Activity Method

For determining the capability of induction of cell proliferation of EGF and its duration, the method comprises the quantification of the absorption of colorant crystal violet by the living cells 3T3 A31.

The preparation of samples of EGF comprises the addition of 100 ml of phosphate saline buffer (PBS1×) to the content of 10 capsules of Example 1, maintaining agitation for 15 minutes. The resultant suspension was centrifuged for 5 minutes at 9000 rpm and the aqueous solution was collected.

Cells 3T3 A31 in 96-plates at a concentration of $1.5 \times 10^5$ cells/mL were sown. These plates were incubated at 37° C., 5% $CO_2$ and 95% humidity for 24 hours.

After completing the incubation time, cells were washed twice with 100 µl of PBS1× and then 100 µl of DMEM 1× without fetal bovine serum (SFB) was added to the medium and plates were incubated at 37° C., 5% $CO_2$ and 95% humidity for another 24 hours.

After completing the incubation time, to the 96-plates dissolutions samples of 100 µl of solutions of EGF at different concentrations and a blank solution of 100 µl of DMEM 1× medium were added. Beginning with the maximum dissolution sample of 100 µl of 10 ng/mL of EGF successively dilutions of 2× were prepared until completing 8 points. The test was made by duplicate. Then, plates were incubated at 37° C., 5% $CO_2$ and 95% humidity for another 24 hours.

After completing the incubation time 50 µL of crystal violet were added and plates were incubated during 3 min. After that, plates were washed with water for discarding the excess of pigment and 50 mL of an aqueous solution of acetic acid at 10% were added to each plate.

The collected data related to the cell count have been processed by the statistical program for parallel lines Parlin V 4.2. The comparison within the dose curve and the response of the reference sample and tested samples were transformed into parallel lines; thereafter it was assigned the biological activity values in UI/mg to the sample preparation, where UI are international units. The potential value assigned to each sample should be between 80-125% of the expected value and the coefficient of geometric variation (CGV) should be equal or less than 20%.

The reference biological activity of the epidermal growth factor before being formulated in form of capsule was $2 \times 10^6$ UI/mg.

TABLE 2

Biological activity of the epidermal growth factor

| Test time (Months) | Biological activity (UI/capsule) | | |
|---|---|---|---|
| | Batch PFCE-1 | Batch PFCE-2 | Batch PFCE-3 |
| 0 | 951786 | 1166618 | 1084094 |
| 3 | 1113113 | 1145395 | 1140876 |
| 6 | 1154034 | 1088190 | 921622 |
| 9 | 1004658 | 1137833 | 952869 |
| 12 | 964330 | 1106933 | 1009456 |
| 18 | 1026334 | 1098926 | 1064994 |
| 24 | 915347 | 1022467 | 1118469 |

As it is shown in the results of Table 2, the biological activity of the EGF after being extracted from capsules with a content of EGF of 0.5 mg is about $1 \times 10^6$ UI/capsule that is $2 \times 10^6$ UI/mg. As the obtained values of Table 2 are equal as the reference value, this fact shows that the EGF maintains its activity after being formulated in form of capsules and even after 24 months of being packaged.

Example 4

Dissolution Profile

The target dissolution profile requires that the EGF is not dissolved under the stomach conditions and that the therapeutic concentration is achieved in the entire colon tract due to its rapid dissolution.

The dissolution test was carried out to a solution of 900 mL at 37° C. and at 100 rpm using a Pharmatest (PTWS, Germany) as a dissolution apparatus according to the conditions described in the USP30 Pharmacopoeia.

Conditions of the Dissolution Bath
Paddle speed: 50 rpm
Temperature of dissolution medium: 37° C.±0.5° C.
Gastroresistant acidic step: 2 hours in HCl 0.1 N
Buffered step: pH 7.0
Vessel volume: 500 mL
Sampling the test solution:
Gastroresistant step: at 1 h and 2 h.
Buffered step: at 10 min, 5 h and 6 h from the beginning of the buffered step.
Conditions of the Chromatographic Analysis
Flux: 2 mL/min
Column: Vydac C8, 250×4.6 (Id: 10531)

Phases: Phase A: 0.1% TFA in water and phase B: 0.05% TFA in ACN
Column temperature: 34° C.
Injection volume: 100 uL
Excitation wavelength: 285 nm
Emitted wavelength: 345 nm
Benefit: 16
Gradient:

| Time (min) | B (%) |
|---|---|
| 0 | 20 |
| 18 | 32.5 |
| 18.5 | 100 |
| 22.5 | 100 |
| 23 | 20 |
| 27 | 20 |

TABLE 3

Dissolution profile of pellets of epidermal growth factor

| pH | Time (hours) | Dissolved EGF (%) |
|---|---|---|
| 1.20 | 2 | 2.4 |
| 7.05 | 4 | 62.3 |
| | 6 | 60.0 |
| | 8 | 60.8 |
| | 10 | 61.3 |

The dissolution profile results in Table 3 show that the pellets of the invention have the required dissolution profile. Thus, the dissolution of the EGF when it is submitted to stomach conditions (pH 1.20) is less than 3% in 2 hours and at least 60% of the EGF after 6 hours is dissolved when it is submitted to colon conditions (pH 7.05). The small variability observed in the percentage of dissolved EGF in the previous Table 3 is due to the fact that these percentages are average values.

Example 5

Stability Studies of EGF Combined with Excipients

The analysis of the content of EGF in solutions of the active ingredient and one excipient or combination of excipients from those mentioned in Example 1 comprises the storage of these solutions of EGF protected from light at 37° C. for 30 days for determining if the above-mentioned excipients unstabilize the EGF by oxidation.

After the storage time, the content of recovered EGF from the solution was calculated by HPLC and the data acquisition was carried out by the program Unicorn version 4.12 (Amersham Biosiences AB, Upsala, Switzerland).

Conditions of the HPLC Analysis
Flux: 0.8 mL/min
Column: Vydac C18, 250×4.6
Porous size of the column: 5 μm
Phases: Phase A: 0.1% TFA in water and phase B: 0.05% TFA in CAN
Detection wavelength: 226 nm
Gradient: From 25 to 45% of solution B in 3 volumes of the column.

TABLE 4

Solutions of EGF with one or more excipients of Example 1

| Samples | EGF (mL) | Talc (g) | Na₂HPO4 (g) | HPMC (g) | LSS (g) |
|---|---|---|---|---|---|
| 1 | 6 | 0.172 | 0.004 | 0.22 | 0.004 |
| 2 | 6 | 0.172 | — | — | — |
| 3 | 6 | — | 0.004 | — | — |
| 4 | 6 | — | — | 0.22 | — |
| 5 | 6 | — | — | — | 0.004 |
| 6 | 6 | 0.172 | 0.004 | — | — |
| 7 | 6 | 0.172 | — | 0.22 | — |
| 8 | 6 | 0.172 | — | — | 0.004 |
| 9 | 6 | — | 0.004 | 0.22 | — |
| 10 | 6 | — | 0.004 | — | 0.004 |
| 11 | 6 | — | — | 0.22 | 0.004 |
| 12 | 6 | 0.172 | 0.004 | 0.22 | — |
| 13 | 6 | 0.172 | 0.004 | — | 0.004 |
| 14 | 6 | 0.172 | — | 0.22 | 0.004 |
| 15 | 6 | — | 0.004 | 0.22 | 0.004 |
| 16 | 6 | — | — | — | — |

TABLE 5

Content of epidermal growth factor in the solutions of Table 4

| | EGF (%) Test time (Days) | | | |
|---|---|---|---|---|
| Samples | 0 | 7 | 15 | 30 |
| 1 | 98.4 | 98.4 | 98.4 | 95.2 |
| 2 | 98.7 | 98.0 | 98.5 | 96.7 |
| 3 | 98.8 | 98.2 | 98.4 | 95.1 |
| 4 | 97.9 | 96.1 | 99.5 | 95.3 |
| 5 | 98.9 | 96.1 | 96.8 | 96.8 |
| 6 | 98.4 | 96.2 | 90.1 | 90.3 |
| 7 | 96.7 | 96.7 | 96.0 | 90.1 |
| 8 | 98.7 | 98.7 | 97.7 | 94.1 |
| 9 | 97.9 | 98.1 | 98.5 | 97.5 |
| 10 | 98.7 | 97.7 | 97.0 | 96.9 |
| 11 | 98.0 | 96.0 | 96.5 | 97.3 |
| 12 | 97.9 | 97.7 | 97.5 | 97.5 |
| 13 | 98.2 | 95.8 | 97.4 | 94.8 |
| 14 | 97.3 | 97.3 | 97.3 | 96.0 |
| 15 | 98.2 | 97.6 | 98.1 | 95.3 |
| 16 | 98.4 | 97.3 | 96.5 | 97.6 |

As it is observed in Table 5, the content of EGF is maintained above 90% by weight even after being in solution for 30 days. As only about 10% of the EGF in the tested solutions was degraded, it is considered that the excipients used for the preparation of the pellets of the present invention are not responsible for the oxidation of the EGF.

Example 6

Process for Manufacturing Capsules of Pellets of Epidermal Growth Factor with an Intermediate Coating Layer 6.1. Process for the Manufacture of the Enteric Coating Pellet with Methionine
The pellet composition is as follow:
Core Pellet

| Ingredients | (%) | Amount (mg/capsule) |
|---|---|---|
| Inert nucleus | 63.79 | 346.18 |
| Epidermal growth factor (EGF) | 0.09 | 0.50 |
| methionine | 0.89 | 4.84 |
| Sodium lauryl sulphate | 0.03 | 0.19 |

-continued

| Ingredients | (%) | Amount (mg/capsule) |
|---|---|---|
| Hydroxypropylmethylcellulose | 2.02 | 10.99 |
| disodium phosphate | 0.03 | 0.19 |
| talc | 2.70 | 14.65 |
| Total core weight | | 69.55 |

Intermediate Coating Layer

| Ingredients | (%) | Amount (mg/capsule) |
|---|---|---|
| Eudragit NE 30D | 5.22 | 28.32 |
| talc | 5.22 | 28.32 |
| Purified water* | | q.s. |
| Total intermediate-coating weight | | 10.44 |

Enteric Coating

| Ingredients | (%) | Amount (mg/capsule) |
|---|---|---|
| Polisorbate 80 | 0.05 | 0.27 |
| Triethylcitrate | 0.11 | 0.60 |
| Sodium lauryl sulphate | 0.11 | 0.60 |
| Talc | 3.94 | 21.38 |
| Eudragit FS30D | 15.79 | 85.69 |
| Purified water* | | q.s. |
| Total enteric-coating weight | 20 | |
| Total functional pellets | 100 | |

"q.s" means "as needed";
*Water removed after processing

In a stainless steel receptacle an aqueous solution of epidermal growth factor was prepared, and methionine with a continuous agitation was added. When the mixture was homogeneous the sodium lauryl sulphate, hydroxypropylmethylcellulose, disodium phosphate and talc were added, maintaining agitation until total dissolution.

1431.83 g of inert nucleus were incorporated in a fluid bed HKC5 and was covered with the solution prepared in advance under the following conditions: air flow: 200 m$^3$/h, diameter of nozzles: 1 mm, spraying pressure: 0.7 bar, spraying ratio of the solution: from 5 to 30 g/min., air temperature: 35° C. and product temperature: 25° C.

Cores thus obtained were then dried in the fluid bed for 1 hour or until the Karl Fisher value is equal or less than 1.5% at a temperature of 35° C. Dry cores were sieved through sieves of 0.425 mm and 0.850 mm.

In a stainless steel receptacle an aqueous homogeneous dispersion of talc and sieved Eudragit NE 30D was prepared. Dry cores were subjected to coating by spraying the aqueous dispersion prepared above in a fluid bed HKC-5. The working conditions were as follows: air flow: 200 m$^3$/h, diameter of nozzles: 1.2 mm, spraying pressure: 0.7 bar, spraying ratio of the dispersion: from 5 to 30 g/min., air temperature: 35° C. and product temperature: 25° C.

The intermediate coating pellets thus obtained were then dried in the fluid bed for 1 hour at a temperature of 35° C. Dry intermediate coating pellets were sieved through sieves of 0.425 mm and 0.850 mm.

In a stainless steel receptacle an aqueous homogeneous solution of Polisorbate 80, triethylcitrate, sodium lauryl sulphate and talc was prepared, maintaining agitation at room temperature until homogeneity total dissolution. Then, in the solution prepared above sieved Eudragit FS30D was added, The intermediate coating layer pellets were subjected to enteric coating by spraying the enteric aqueous suspension prepared above in a fluid bed HKC-5. The working conditions were as follows: air flow: 200 m$^3$/h, diameter of nozzles: 1.2 mm, spraying pressure: 0.7 bar, spraying ratio of the solution: from 5 to 30 g/min., air temperature: 35° C. and product temperature: 25° C.

The enteric coating pellets thus obtained were then dried in the fluid bed for 1 hour or until the Karl Fisher value is equal or less than 1.5% at a temperature of 35° C. Dry enteric coating pellets were sieved through sieves of 0.425 mm and 0.850 mm.

6.2. Process for the Manufacture of Capsules of Pellets of Epidermal Growth Factor Comprising the Intermediate Coating Layer and Methionine Hard capsules made of gelatin or hydroxypropylmethylcellulose with the enteric coating pellets of Example 6 section 6.1. were filled using a Bosch Zanassi automatic capsule-filling machine.

Example 7

Dissolution Profile of Pellets of Epidermal Growth Factor Comprising the Intermediate Coating Layer The dissolution test was carried out as it is disclosed in Example 4.

The dissolution of the EGF when it is submitted to stomach conditions (pH 1.20) is less than 3% in 2 hours and at least 60% of the EGF after 6 hours is dissolved when it is submitted to colon conditions (pH 7.05). Thus, pellets which comprise the intermediate coating layer of the invention have the required dissolution profile.

PRIOR ART REFERENCE MENTIONED IN THE APPLICATION

1. US 2007/26082

The invention claimed is:

1. An orally administrable pharmaceutical pellet which comprises a core and an enteric coating, wherein the core comprises a pharmaceutically effective amount of epidermal growth factor and a sulphur-containing antioxidant selected from the group consisting of methionine and $K_2S_2O_7$, where the molar ratio between the epidermal growth factor and the antioxidant is from 1:10 to 1:670; and the core comprises:
   60-80% by weight of an inert nucleus;
   0.05-1% by weight of the epidermal growth factor;
   0.5-3% by weight of the sulphur-containing antioxidant selected from the group consisting of methionine and $K_2S_2O_7$;
   0.02-0.07% by weight of surfactant;
   1.5-5% by weight of binder;
   0.02-0.07% by weight of alkaline agent; and
   2-5% by weight of glidant
where the binder is hydroxypropylmethyl cellulose.

2. The pellet according to claim 1, where the alkaline agent is disodium phosphate.

3. The pellet according to claim 1, where the glidant is talc.

4. The pellet according to claim 1, where the surfactant is sodium lauryl sulphate.

5. The pellet according to claim 1, where the core comprises:
   69% by weight of the inert nucleus;
   0.10% by weight of the epidermal growth factor;
   1.3% by weight of methionine;

0.05% by weight of sodium lauryl sulphate;
2% by weight of hydroxypropylmethylcellulose;
0.05% by weight of disodium phosphate; and
4% by weight of talc.

6. The pellet according to claim 1, where the core comprises:
69% by weight of the inert nucleus;
0.10% by weight of the epidermal growth factor;
2% by weight of $K_2S_2O_7$;
0.05% by weight of sodium lauryl sulphate;
2% by weight of hydroxypropylmethylcellulose;
0.05% by weight of disodium phosphate; and
4% by weight of talc.

7. The pellet according to claim 1, where the enteric coating comprises poly(methacrylic acid/methylacrylate/methyl methacrylate), triethylcitrate, sodium lauryl sulphate, talc or mixtures thereof.

8. The pellet according to claim 1, further comprising an intermediate coating layer which comprises at least a modified release polymer.

9. The pellet according to claim 8, where the intermediate coating layer further comprises a glidant.

10. The pellet according to claim 8, where the modified release polymer is selected from the group consisting of polyacrylates, polymethacrylates, ethylcellulose, hydroxypropylcellulose, hydroxypropylmethylcellulose, and mixtures thereof.

11. The pellet according to claim 10, where the modified release polymer is a polymer of poly(ethyl acrylate/methylmethacrylate) esters.

12. The pellet according to claim 9, where the glidant is talc.

13. A process for the preparation of the pellet as defined in claim 1, which comprises:
(a) coating of the inert nucleus to form an active layer by spraying an aqueous suspension which comprises the epidermal growth factor, the antioxidant, the surfactant, the binder, the alkaline agent and the glidant;
(b) drying the active layer formed in step (a);
(c) coating the nucleus of step (b) to form a coated pellet by spraying a suspension comprising the enteric coating, wherein the enteric coating comprises an enteric coating polymer and a pharmaceutically acceptable excipient; and
(d) drying the coated pellet formed in step (c);
where the temperature of each step of the process is up to 40° C.

14. The process according to claim 13, for the preparation of a pellet further comprising an intermediate coating layer which comprises at least a modified release polymer and a pharmaceutically acceptable excipient, the process further comprising an additional step of coating the nucleus obtained in step (b) by spraying a suspension which comprises the modified release polymer and the pharmaceutically acceptable excipient; and drying the layer formed.

15. A pharmaceutical capsule which comprises a pellet as defined in claim 1.

16. A method of treating ulcerative colitis which comprises administering to mammals in need of such treatment an effective amount of the pellet as defined in claim 1.

* * * * *